United States Patent [19]

Knecht

[11] Patent Number: 4,612,310

[45] Date of Patent: Sep. 16, 1986

[54] ANTIRHEUMATICALLY ACTIVE SUPPOSITORIES

[75] Inventor: Adolf Knecht, Freiburg, Fed. Rep. of Germany

[73] Assignee: Warner-Lambert Company, Morris Plains, N.J.

[21] Appl. No.: 768,297

[22] Filed: Aug. 19, 1985

[30] Foreign Application Priority Data

Sep. 29, 1984 [DE] Fed. Rep. of Germany ....... 3435843

[51] Int. Cl.$^4$ .......................................... A61K 31/54
[52] U.S. Cl. .................................. 514/222; 514/965; 514/966
[58] Field of Search ......................... 514/965, 966, 222

[56] References Cited

PUBLICATIONS

Chem. Abst. 102, 209229a (1985).

*Primary Examiner*—Stanley J. Friedman
*Attorney, Agent, or Firm*—Ronald A. Daignault

[57] ABSTRACT

Antirheumatically active suppositories with comparable bioavailability to oral or parenteral preparations are described, which contain a salt of a compound of general Formula I

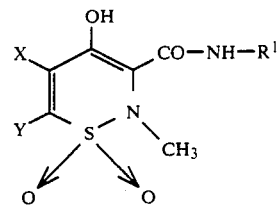

in which $R^1$ represents a heterocyclic ring and X together with Y an annelated aromatic ring; and an organic base of the general Formula II

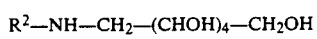

in which $R^2$ represents a hydrogen atom or an alkyl group with one to six carbon atoms, especially a methyl, ethyl, or propyl group; in a usual suppository base, are described.

5 Claims, No Drawings

ANTIRHEUMATICALLY ACTIVE SUPPOSITORIES

DESCRIPTION

Nonsteroidal antirheumatics are normally used in therapy not only in oral dosage forms (capsules, tablets), but also in parenteral and especially rectal dosage forms.

In order to attain adequate bioavailability with oral or rectal drug preparations, the rate at which the active ingredient passes into solution is of decisive importance.

Substances with the basic oxicam structure, such as piroxicam or isoxicam, which have proved to be extremely successful in therapy, are distinguished by only low solubility in water. At the same time the individual dose to be administered is relatively high, e.g., between 100 and 300 mg in the case of isoxicam, so that it is difficult to guarantee the required bioavailability galenically.

In the case of oral formulations high bioavailability can be attained by suitable formulations. The relative bioavailability, compared with parenteral dosage forms as standard, is extremely high at 90%, but it must be remembered that relatively large amounts of liquid are available in the gastro-intestinal tract for the dissolution of the drug after oral administration.

In the case of rectal application forms, however, the conditions prevailing are entirely different. Isoxicam, processed to suppositories in conventional triglyceride bases, has much lower bioavailability than would at first be expected. Additions of surface-active substances or the use of hydrophilic carriers only effect gradual improvement of the bioavailability. In no case, however, plasma levels are attained which are comparable with those after oral administration of equal doses.

This can be explained by the fact that normally only very limited amounts of liquids are available in the rectum and the conditions for absorption are therefore considerably worse than in the gastro-intestinal tract after oral administration.

From U.S. Pat. No. 4,482,554 it is known that by the use of methylglucamine in greater than stoichiometric amounts isoxicam can be brought into stable solutions for parenteral application, if a water-miscible solvent, e.g., polyethylene glycol, is added at the same time. On the other hand, solutions which according to European Patent Specification No. 2482 contain methyl glucamine in stoichiometric proportion to the drug do not possess satisfactory stability when isoxicam is used, because aqueous solutions of the stoichiometric salt exhibit recrystallization after a short time, when the sparingly soluble isoxicam is precipitated. With regard to the use of the stoichiometric salt in rectal dosage forms it was therefore to be expected that, compared with the conditions prevailing in the gastro-intestinal tract, a worse situation because of smaller available volume of liquid for the dissolution of the drug and proportional reduction of the bioavailability as a result of partial precipitation of the sparingly soluble isoxicam in the rectum would exist.

It was surprisingly found that the stoichiometric salt of isoxicam and N-methylglucamine, incorporated into triglyceride suppository bases, can be processed to suppositories, which in in vivo experiments in humans show bioequivalence with oral forms (capsules or tablets). Both plasma level maxima and areas under the plasma level curves after rectal administration do not differ significantly from the values obtained for oral administration.

With the very small volume of liquid available in a human rectum it could not be expected that an equal amount of the slat of a drug which at neutral pH is soluble in water only to the extent of 0.04 mg/ml would be available for absorption per unit time as after oral administration of the same dose of the drug.

Thus, it is possible to incorporate the extremely sparingly soluble drug isoxicam into a rectal dosage form which can be introduced into therapy at the same dosage as the established oral dosage form.

Accordingly the present invention is a suppository comprising a usual suppository base as an antirheumatic active ingredient, in which the active ingredient consists of a salt containing approximately equimolar amounts of a compound of the formula (I)

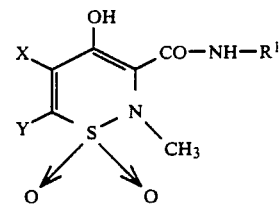

in which $R^1$ represents a heterocyclic ring, e.g., pyridine or 5-methyl-3-isoxazole and X together with Y a condensed aromatic ring, e.g., a benzene or thiophene ring; and an organic base of general formula (II)

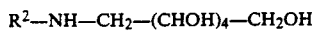

in which $R^2$ represents a hydrogen atom or an alkyl group with one to six carbon atoms, especially a methyl, ethyl, or propyl group.

Preferably a salt is used which contains the compound of Formula I and the organic base of Formula II in the exact ratio 1:1.

Especially preferred is the methylglucamine salt of isoxicam.

A usual suppository base means both hydrophilic substances, such as soap gels, glycerine gelatins or physiologically acceptable polymers, e.g., polyvinylpyrrolidones or polyethylene glycols, and hydrophobic substances, such as fats and their esters or alcohols and their esters, tallow, waxes, or oils and their hydrogenated fractions. In addition mixtures of these substances are used which may also contain further additions such as metal soaps, salts of organic acids of carbohydrates.

The preferred substances for the preparation of the suppositories are triglycerides.

The present invention also includes a method of treating rheumatoid arthritis which comprises administering to a patient a suppository containing an effective amount of active ingredient together with a suppository base.

A further subject of the invention is a process for the preparation of suppositories in which the desired amount of active ingredient is ground and melted together with neutral oil and hard fat. After homogenization the suppository base which has been cooled to about 36° C., is poured into cooled molds.

Preferably the amount of isoxicam-meglumine used is such that the preparation contains 322 mg per suppository. Assuming a water content of the isoxicam-methylglucamine of 2.06%, this corresponds to a content of 200 mg of isoxicam per suppository.

The following examples are intended to serve as more detailed illustrations of the invention.

EXAMPLE 1

For the preparation of 10,000 suppositories each containing 200 mg of the active ingredient isoxicam 2.0 kg of the finely crystalline drug and 4.0 kg of lactose are worked up with 15.0 kg of hard fat DAB which has been melted at a maximum of 50° C. The mixture is then homogenized using a sprocket-wheel colloid mill. The melt is adjusted to 35° C. and poured into cooled molds.

In comparative bioavailability tests suppositories of this composition showed average relative bioavailability of only 50% compared with isoxicam capsules containing 200 mg of the drug.

EXAMPLE 2

For the preparation of 10,000 suppositories according to the invention 3.22 kg of group isoxicam-meglumine and 950 g of neutral oil are worked up with 15.7 kg of hard fat DAB (molten). The mixture is homogenized using a sprocket-wheel colloil mill, cooled to about 36° C. and molded into suppositories in cooled molds. Each of these suppositories contains 322 mg of isoxicam-meglumine (water content 2.06%), corresponding to 200 mg of isoxicam.

In a comparative bioavailability study these suppositories showed comparable plasma level maxima and comparable areas under the plasma level curve with 200 mg of isoxicam administered orally.

I claim:

1. A therapeutic supository composition comprising a triglyceride suppository base and an antirheumatically active ingredient, in which the active ingredient consists of a salt containing approximately equimolar amounts of a compound of the formula

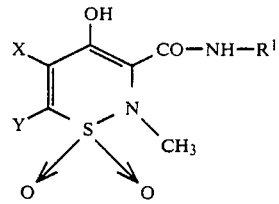

in which $R^1$ represents pyridine or 5-methyl-3-isoxazole and X together with Y forms a benzene or thiophene ring; and an organic base of the formula

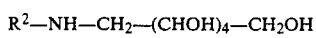

$$R^2-NH-CH_2-(CHOH)_4-CH_2OH$$

in which $R^2$ represents a hydrogen atom or an alkyl group with one to six carbon atoms.

2. A composition according to claim 1 which contains isoxicam as the active ingredient.

3. A composition according to claim 1 which contains methylglucamine as the base.

4. A composition according to claim 1 which contains 100 to 300 mg of the active ingredient.

5. A method of treating rheumatoid arthritis which comprises administering to a patient an effective amount of suppository as claimed in claim 1.

* * * * *